United States Patent [19]

Wolff

[11] 4,095,113

[45] June 13, 1978

[54] APPARATUS FOR PRODUCING ULTRAVIOLET RADIATION

[76] Inventor: Friedrich Wolff, Bertholdstrasse 18, Frankfurt, Germany

[21] Appl. No.: 716,253

[22] Filed: Aug. 20, 1976

[30] Foreign Application Priority Data

| Aug. 26, 1975 | Germany | 2537855 |
| Jan. 30, 1976 | Germany | 2603460 |
| Feb. 12, 1976 | Germany | 2605487 |
| May 31, 1976 | Germany | 2624297 |

[51] Int. Cl.² .............................................. G01J 1/00
[52] U.S. Cl. ................................... 250/494; 250/504; 250/510
[58] Field of Search ............... 128/371, 372, 373, 503, 128/504, 510, 455, 456, 494

[56] References Cited

U.S. PATENT DOCUMENTS

| 828,733 | 8/1906 | Fuller | 128/371 |
| 1,256,522 | 12/1918 | Croxton | 250/503 |
| 1,583,420 | 5/1926 | Pichard | 128/371 |
| 2,184,644 | 12/1939 | Homberger | 128/371 |
| 2,356,592 | 8/1944 | Kolbert et al. | 250/504 |
| 2,631,588 | 3/1953 | Paschell | 250/455 |
| 2,733,351 | 1/1956 | Vogel | 250/503 |
| 3,084,258 | 4/1963 | Furedy | 250/494 |
| 3,271,786 | 9/1966 | Joy | 128/371 |
| 3,381,289 | 7/1972 | Knight | 250/504 |
| 3,483,871 | 12/1969 | Wilson | 128/372 |

*Primary Examiner*—Bruce C. Anderson
*Attorney, Agent, or Firm*—Peter K. Kontler

[57] ABSTRACT

Apparatus for treatment of humans with ultraviolet rays has one or more mercury lamps, Xenon lamps or other radiation sources and associated reflectors which establish a high-density radiation field in close proximity to the exit opening or openings. The radiation is filtered so that the body of a person located in the region of the high-density field is exposed only to rays in the range of 315 to 400 nanometers. The heat energy output of the radiation source or sources is sufficiently low to enable a person to stand long periods of uninterrupted exposure to radiation in the range of 315 to 400 nm so that a tanning effect can be achieved as a result of a single continuous exposure for a requisite interval of time. Alternatively, the apparatus is equipped with suitable heat absorbing and intercepting means, especially if the radiation source or sources are high-pressure mercury lamps or Xenon lamps. The apparatus can constitute a table model, a floor model, a ceiling model, a wall model or a combination of these.

39 Claims, 17 Drawing Figures

APPARATUS FOR PRODUCING ULTRAVIOLET RADIATION

BACKGROUND OF THE INVENTION

The present invention relates to radiation producing apparatus in general, and more particularly to improvements in apparatus which can be used for tanning of human skin and/or for therapeutical purposes. Still more particularly, the invention relates to apparatus (popularly known as sunlamps) which are designed to produce and orient infrared and/or ultraviolet radiation. Such apparatus comprise one or more radiation sources (e.g., ultraviolet lamps), one or more reflectors and means (including or constituting the reflector or reflectors) which defines one or more exit openings for radiation.

Sunlamps are often classified according to the dimensions of the radiation field. Thus, a table model is normally designed for directing radiation against selected areas (especially the face and the upper part of the torso) of the human body, and a floor, wall or ceiling model is normally (but not invariably) designed to direct radiation against the entire body. Sunlamps of the type capable of producing radiation fields which are large enough to effect simultaneous tanning of all parts of a human body are sometimes called solaria. As a rule, a person who is about to acquire artificial tan by using a table model must be positioned at a distance of 60 to 100 centimeters from the exit opening of the sunlamp. In a solarium, whose radiation source or sources are normally installed at a level above a bunk, couch, cot or bed, the prescribed distance from the exit opening is in the range of 120 to 200 centimeters. A table model frequently comprises a single radiation source, and a solarium comprises several (often three) radiation sources, especially in the form of high-pressure discharge lamps for ultraviolet radiation. The output of radiation sources for table models is 100 to 150 watts, 150 to 200 watts for relatively small solaria (normally for use in private homes), and 350 to 500 watts for use in giant solaria.

A sunlamp is used primarily to produce a sun-tanning effect. However, before a conventional lamp produces a discernible tanning effect, ultraviolet radiation causes many other (mostly undesirable biological effects, such as reddening of the skin (sunburn) which entails flaking and hardening of the skin. Since the minimum dosage of ultraviolet radiation which produces sunburn is reached within minutes (especially if the density of the radiation field in the region of exposed skin is high), i.e., well before the skin begins to exhibit even a slight trace of tanning, the exposure of skin to ultraviolet radiation must be repeated again and again whereby the duration of exposure normally increases from treatment to treatment. However, even the just described mode of using a sunlamp cannot produce a deep tan such as is acquired by prolonged exposure to sun rays.

SUMMARY OF THE INVENTION

An object of the invention is to provide a novel and improved apparatus for producing ultraviolet radiation, especially a sunlamp, which is constructed and assembled in such a way that a person desiring to acquire a pronounced tan must undergo a relatively small number of treatments or a single treatment.

Another object of the invention is to provide an apparatus which is capable of producing a pronounced tan without sunburn and/or other undesirable effects which are unavoidable consequences of the utilization of conventional sunlamps.

A further object of the invention is to provide an apparatus which can be used in commercial or other establishments or in homes, which is of eye-pleasing appearance, and which can be used by fair-skinned persons without any danger of sunburn or other unpleasant effects which develop as a result of exposure to radiation produced by conventional sunlamps.

An additional object of the invention is to provide a novel assembly of radiation source or sources and one or more reflectors for use in the improved sunlamp.

An ancillary object of the invention is to provide an apparatus whose heat energy output is sufficiently low to permit long-lasting exposure of human skin to ultraviolet radiation without any discomfort to the person or persons using the apparatus.

Another object of the invention is to provide novel and improved radiation filters for use in the above outlined apparatus.

An additional object of the invention is to provide an apparatus which can be designed as a table model, a floor model, a ceiling model or a wall model and which can be used by a single person or simultaneously by two or more persons.

A further object of the invention is to provide an apparatus whose exit opening or openings for ultraviolet radiation can be placed into immediate or close proximity to the skin without any danger of sunburn or other undesirable biological effects.

Another object of the invention is to provide novel and improved means for supporting one or more apparatus of the above outlined character.

One feature of the invention resides in the provision of an apparatus for producing ultraviolet radiation, particularly a sunlamp, which comprises at least one high- or low-pressure mercury vapor lamp or another suitable source of ultraviolet radiation, reflector means associated with the source or sources to define therewith at least one exit opening for ultraviolet radiation as well as to establish a high-density radiation field of predetermined area in or close to the region of the exit opening or openings, and suitable filter means for intercepting at least the major percentage of predetermined wavelength bands of ultraviolet radiation ahead of the field so that the field consists essentially of the remaining wavelength band of ultraviolet radiation, preferably between 315 and 400 nanometers.

If the source or sources are such that the emission of ultraviolet radiation is accompanied by the generation of substantial quantities of heat energy, the apparatus further comprises heat absorbing or intercepting means which is interposed between the source or sources and the field to maintain the temperature of the region of the field within a range which is below the range of discomfort to the person or persons whose skin or skins are exposed to radiation. Alternatively, the source or sources may include one or more lamps whose heat energy output is sufficiently low to insure that the temperature in the region of the radiation field is within the aforementioned range (i.e., within a range below the range of discomfort to the person or persons whose skin or skins are exposed to radiation).

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
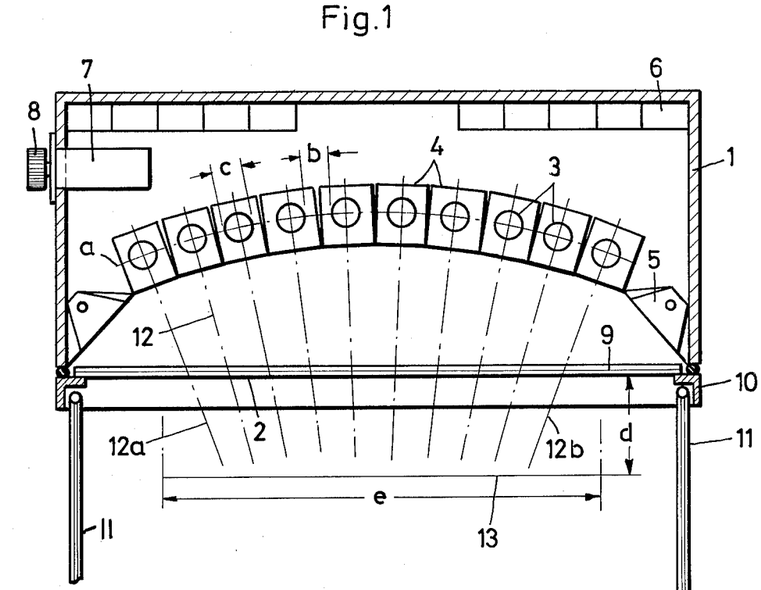
FIG. 1 is a horizontal sectional view of an apparatus with a battery of ten upright radiation sources which embodies one form of the invention.

FIG. 1 shows an apparatus which comprises a housing 1 the front side of which has an exit opening or window 2 for ultraviolet radiation. The housing 1 contains a battery of ten parallel upright rod-shaped radiation sources 3 (hereinafter called sources) whose axes are located in an arcuate plane $a$. Each source 3 is assumed to be a low-pressure mercury lamp having a length of 150 centimeters and an output of 65 to 120 watts, preferably closer to 120 watts. Each source 3 is associated with a trough-shaped reflector 4 of the type shown in FIG. 2 (or with one of other types of reflectors disclosed in my copending application Ser. No. 716,254 filed Aug. 20, 1976 and entitled "Reflector for use in sunlamps or the like").

The battery of sources 3 and reflectors 4 is flanked by two infrared heaters 5 which are optional. These heaters can be used alternatively with the sources 3. Each heater 5 may comprise an electrically heated rod consisting of silicon carbide.

The housing 1 further contains auxiliary equipment 6 (e.g., timers and chokes) and controls 7 including a starter knob 8 which is accessible at the exposed side of the left-hand side panel of the housing. Each source 3 comprises a tubular (preferably cylindrical) envelope 3a (see FIG. 2) made of glass which constitutes a filter by intercepting predetermined wavelength bands of ultraviolet radiation while permitting the remaining band to reach the window 2. The envelopes intercept all or nearly all radiation within the so-called UVC range ("far" region) of 200 to 280 nm (nanometers) and within the so-called UVB range ("Dorno" region) of 280 to 315 nm, but do not intercept radiation within the so-called UVA range ("near" region) of 315 to 400 nm.

The window 2 contains a pane 9 and the housing 1 further comprises a frame 10 for the window 2 as well as doors 11 which are pivotable between the illustrated (open) positions in which the window 2 is exposed and closed positions in which they conceal the window. It will be noted that the housing 2 contains all essential components of the apparatus; this housing may resemble a cabinet, e.g., a cabinet resembling the housing of a television receiver, which is of eye-pleasing appearance not only when in use but also when the doors 11 are closed. The doors 11 and/or other parts of the housing 1 can be provided with suitable ornamentation to further enhance the appearance of the apparatus.

The distance $b$ between neighboring sources 3 in the housing 1 may equal or approximate 70 percent of the diameter $c$ of a source. Thus, the distance between the central symmetry planes 12 of neighboring sources 3 equals $b+c$. The symmetry planes 12 are normal to the plane $a$. The symmetry planes 12a and 12b of the two outermost sources 3 make an angle of less than 80°, for example, 45°.

The assembly of sources 3 and reflectors 4 establishes a high-density radiation field 13 in front of the pane 9. The distance $d$ between the window 2 and the field 13 is assumed to equal or approximate 10 centimeters. The width $e$ of the field 13 is assumed to be 70 centimeters and its height (as considered at right angles to the plane of FIG. 1) is 150 centimeters (i.e., it matches the length of a rod-shaped source 3). The apparatus of FIG. 1 produces a high-density field 13 because the distance between the sources 3 and the field is very small, because of the substantial number of sources 3, because of the aforementioned output (65 to 120 watts) of the sources, and also due to the fact that the axes of the sources 3 are located in a common plane whose concave side faces the window 2. The high density of the field 13 is further attributable to the improved design of the reflectors 4 which are disclosed and claimed in the aforementioned copending application Ser. No. 716,254. The density of the field 13 may equal or approximate 12 mw/cm². As a rule, the density decreases in a direction from the center of the window 2 toward the doors 11 (i.e., toward the vertical marginal portions of the field); however, the minimum density in the region of such marginal portions is still much higher than 4 mw/cm².

It is clear that the axes of sources 3 may be placed into a plane which is exactly parallel to the plane of the pane 9, or that the battery of sources 3 may be arrayed in another formation, e.g., the sources may form a zig-zag array each section of which includes two, three or even more parallel sources.

The apparatus of FIG. 1 is not only simple but also very compact and relatively inexpensive. Its energy requirements are low. For example, the plug of its electric cable (not shown) can be inserted into a household outlet of a circuit which is secured by a 10-ampere fuse.

The number of sources 3 in the apparatus of FIG. 1 can be reduced below or increased above ten. For example, the number of sources may be anywhere between five and twenty, preferably ten to twelve. The UVA-radiation output of each source 3 is preferably at least 5 watts per meter of the source. The heat energy output of low-pressure mercury lamps is so low that an entire battery of such lamps can be used in the apparatus of FIG. 1 without causing any discomfort to a person standing very close to the window 2. Since the UVA-radiation output of a low-pressure mercury lamp is very low, such lamps are preferably placed very close to each other and each reflector 4 preferably surrounds the respective lamp from three sides to insure that a very high percentage of UVA radiation is caused to form a high-density field at or close to the window 2. The length and width of the field 13 can be selected at will, i.e., by the simple expedient of selecting a requisite number of radiation sources having a desired length.

Since the tanning effect is produced more rapidly if the UVA-radiation output of the sources is relatively high, it is desirable to select low-pressure mercury lamps with a relatively high output (at least 8 watts per meter) of UVA radiation. Many recent types of such lamps have an output of at least 10 w/m.

If the apparatus is to be used for simultaneous exposure of the entire body to radiation in the optimum band of ultraviolet light, the length of sources 3 preferably exceeds 100 centimeters and most preferably 150 centimeters. Such sources are economical because the necessary firing potential is relatively low and the apparatus must embody a relatively simple and inexpensive auxiliary equipment. The optimum length of sources which are used in a solarium (for simultaneous exposure of all parts of the body of an adult to ultraviolet radiation) is approximately 180 centimeters.

The overall output of conventional rod-shaped radiation sources having a length of 150 centimeters and being capable of furnishing satisfactory radiation in the UVA band is at least 100 watts, normally 120 watts. By appropriate treatment, the overall output of such sources can be reduced to 80 watts without reducing their output in the UVA band of ultraviolet radiation.

The selected spectral data (especially as regards the UVA radiation output) should not fluctuate during treatment. Since a shift normally takes place in response to changes in temperature, the presently known sunlamps often or invariably employ blowers or other suitable cooling means. Such cooling means can be omitted if the radiation sources 3 are low-pressure mercury lamps containing a chemical additive (e.g., amalgam) which is capable of insuring a constant UVA radiation output and a constant relative spectrum independently of temperature changes.

The density of the field 13 in front of the window 2 is enhanced by placing the radiation sources 3 close to each other. As a rule, the distance $b$ between two neighboring sources 3 should not exceed (and is preferably less than) the diameter $d$ of a source.

Figure 2:
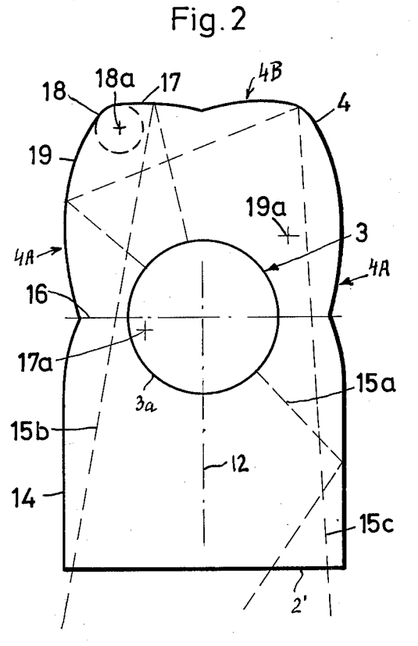
FIG. 2 is an enlarged view of a detail in FIG. 1, showing one of the radiation sources and the associated reflector.

FIG. 2 shows one of the rod-like low-pressure mercury lamps 3 and the associated trough-shaped reflector 4. The reflector 4 comprises two side walls 4A with substantially parallel front portions 14 and rear portions 19 having concave inner surfaces facing each other, a rear wall 4B having two portions 17 which are mirror symmetrical to each other with reference to the plane 12 and include concave front surfaces facing the rear side of the source 3, and two relatively narrow intermediate walls 18 having concave inner surfaces which merge into the inner surfaces of the respective rear portions 19 as well as into the inner surfaces of the respective portions 17 of the rear wall 4B. The center of curvature of the front surface of the left-hand portion 17 of the rear wall 4B is shown at 17a, the center of curvature of the inner surface of the left-hand intermediate wall 18 is shown at 18a, and the center of curvature of the inner surface of the left-hand rear portion 19 is shown at 19a. The radii of curvature of the front surfaces of portions 17 may but need not equal the radii of curvature of the inner surfaces of rear portions 19, and each such radius is several times the radius of curvature of the inner surface of the left-hand or right-hand intermediate wall 18. The reflector 4 has two identical halves which are mirror symmetrical to each other with reference to the plane 12, i.e., to a plane which includes the axis of the source 3 and halves the rear wall 4B. The exit opening for radiation is shown at 2'; this opening extends between the foremost parts of front portions 14 of the side walls 4A, and such front portions preferably extend at least slightly beyond the foremost part of the source 3 so that the entire source 3 is fully received in the space between the side walls 4A and rear wall 4B. The side walls 4A define with the source 3 two relatively narrow gaps or clearances 16 for the passage of rays toward the exit opening 2'. The inner surfaces of the front portions 14 of side walls 4A may but preferably do not diverge from each other in a direction toward the exit opening 2'. Rays 15a which issue from the front part of the source 3 and impinge upon the inner surfaces of the front portions 14 are reflected into the exit opening 2', i.e., toward the field 13 of FIG. 1. The aforediscussed configuration of the rear portions 19 of the side walls 4A, of the rear wall 4B and of the intermediate walls 18 insures that a very high (normally by far the major) percentage of rays issuing from the rear side of the source 3 is reflected into the gaps 16 and thence into the exit opening 2'. As shown in FIG. 2, a ray 15b which impinges upon the left-hand portion 17 of the rear wall 4B can be reflected directly into the left-hand gap 16. A ray 15c which issues from the rear portion of the source 3 and impinges upon the left-hand rear portion 19 is reflected against the right-hand intermediate wall 18 which reflects the ray 15c into the right-hand gap 16. The rear portions 19 of the side walls 4A may merge gradually into the respective front portions 14 or (see FIG. 2) the side walls 4A may be formed with pronounced internal ridges which are adjacent to narrowest portions of the respective gaps and constitute the loci where the foremost parts of the rear portions 19 meet the rearmost parts of the respective front portions.

The aforedescribed configuration of the walls 4A, 18, 18 and 4B contributes to the density of the radiation field 13 because the concave surfaces of these walls are capable of directing into the gaps 16, and thence into the exit opening 2', all or nearly all rays which issue from the rear side of the source 3, i.e., from that side which is located rearwardly or inwardly of the narrowest portions of the gaps 16.

Figure 3:
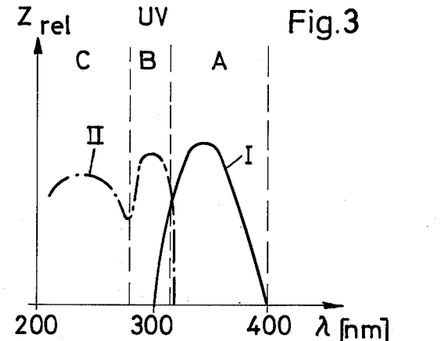
FIG. 3 is a diagram whose curves denote the sensitivity of human skin to sunburn and the tanning effect upon human skin in different bands of ultraviolet radiation.

In the coordinate system of FIG. 3, the wavelength lambda of ultraviolet radiation issuing from the source 3 is measured along the abscissa and the relative sensitivity $Z_{rel}$ of human skin to ultraviolet radiation of different wavelengths is measured along the ordinate. The wavelength is measured in nm (nanometers). The ultraviolet radiation range is between 200 and 400 nm. The band between 200 and 280 nm (the aforementioned UVC band) is followed by the so-called UVB band between 280 and 315 nm, and the UVB band is followed by the UVA band between 315 and 400 nm.

The solid-line curve I of FIG. 3 shows the variations of tanning effect of ultraviolet radiation upon the human skin as a function of wavelength. It will be noted that the tanning effect is produced by radiation in the band UVA and in the right-hand portion of the band UVB (between 300 and 400 nm), and that such effect is most pronounced at 340 nm. The phantom-line curve II of FIG. 3 is representative of relative sensitivity of human skin to sunburn as a function of wavelength. The sensitivity curve II has a peak (at 297 nm) in the UVB band and ends in the UVA band (at 320 nm). The sensitivity of human skin to sunburn in the band UVA is practically nil. In accordance with a feature of the invention, ultraviolet radiation in the bands UVC and UVB is intercepted (either entirely or to a very high degree) by the tubular envelope of the source 3 and/or by a filter (e.g., the pane 9 of FIG. 1) which is installed between the exit openings 2' of the reflectors 4 and the field 13 of FIG. 1. This insures that the field 13 consists practically exclusively of radiation in the UVA band, i.e., in a band which does not cause any sunburn but is most effective for rapid tanning of human skin. Therefore, the person using the improved apparatus can receive high dosages of radiation during a long and uninterrupted interval of time to insure pronounced tanning without any danger of sunburn. In order to produce a tanning effect, the radiation must exceed a threshold value of 7.5 to 10 w/cm$^2$; such threshold value can be reached and exceeded within a relatively short interval of continuous exposure to radiation in the field 13.

Figure 4:
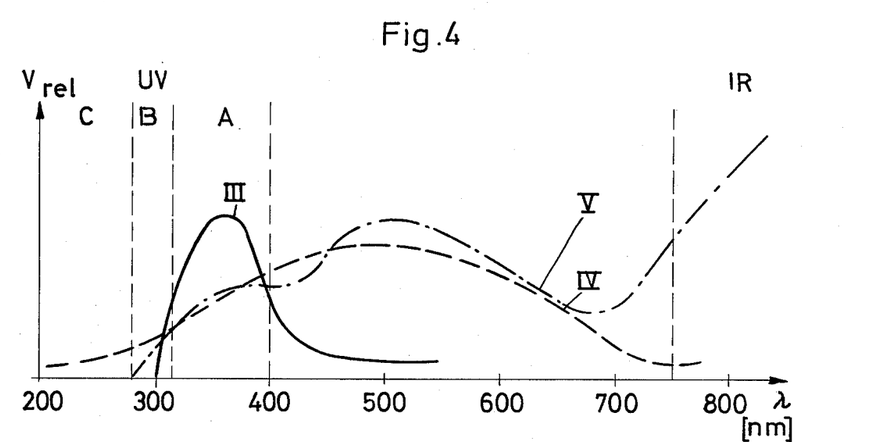
FIG. 4 is a similar diagram showing the emission of radiation in the ultraviolet, visible and infrared ranges by resorting to different types of radiation sources.

In the coordinate system of FIG. 4, the wavelength (lambda) of radiation is measured along the abscissa (in nm) and the relative distribution $V_{rel}$ of radiation density is measured along the ordinate. The solid-line curve III represents the density of radiation furnished by a low-pressure mercury lamp at different wavelengths. The low-pressure lamp is assumed to have been subjected to special treatment to increase the output of radiation in the UVA band (315–400 nm). It will be noted that the curve III has a pronounced peak in the UVA band. The broken-line curve IV represents similar characteristics of a high-pressure mercury lamp which was subjected to special treatment to increase the output in the range of ultraviolet light. The phantom-line curve V represents similar characteristics of a Xenon lamp. It will be seen that the output of a low-pressure mercury lamp is most satisfactory in the UVA band of ultraviolet light; this is in contrast to the output of a high-pressure mercury lamp or a Xenon lamp. However, the output of a high-pressure mercury lamp or a Xenon lamp can greatly exceed the output of a low-pressure mercury lamp which, in turn, enables the high-pressure mercury lamps and Xenon lamps to supply large quantities of ultraviolet radiation in spite of the fact that they are more effective in the range of visible and/or infrared light.

Figure 5:
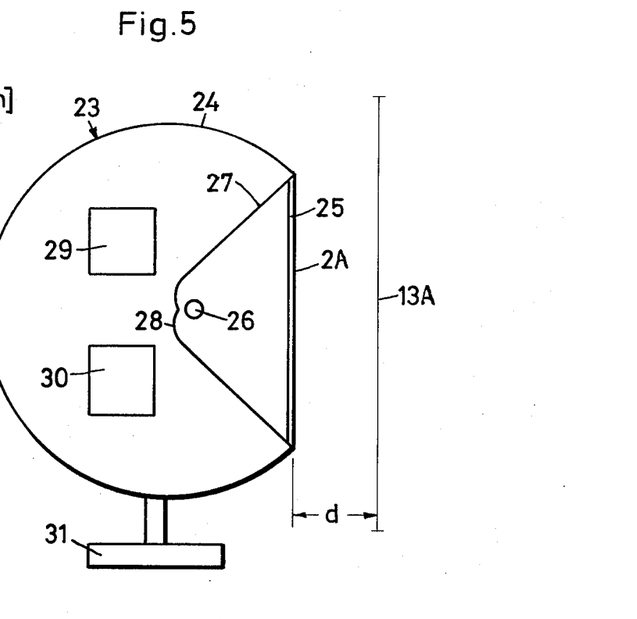
FIG. 5 is a schematic partly side elevational and partly vertical sectional view of a second apparatus.

FIG. 5 shows an apparatus 23 which is a table model and includes a hollow spherical housing 24 mounted on a suitable pedestal 31, preferably in such a way that the user can change the angular position and/or the inclination of an exit opening 2A. The exit opening 2A receives a plate-like filter 25 for UVB and UVC bands of ultraviolet radiation. The material of the filter 25 is assumed to be such that it intercepts all or nearly all radiation having a wavelength between 200 and 315 nm.

The housing 24 contains a horizontal rod-shaped high-pressure mercury lamp 26 located between the exit opening 2A and the rear wall 28 of a reflector 27. The length of the source 26 is 20 centimeters, and its output is assumed to be in the range of 1,000 to 2,000 watts. It is further assumed that the source 26 has been subjected to a special treatment to increase the radiation output in the UVA band. The part 26 can be said to constitute a substantially point-shaped source of ultraviolet radiation.

The reflector 27 is a substantially bowl-shaped wide-angle reflector whose rear wall 28 is closely adjacent to the rear side of the source 26 and whose divergent side walls extend all the way to the exit opening 2A. The configuration of the rear wall 28 of the reflector 27 is somewhat similar to that of the rear wall 4B shown in FIG. 2. A high-density radiation field 13A develops at a distance d from the exit opening 2A. The development of such high-density field is attributable, at least to a substantial extent, to the fact that the rear wall 28 of the reflector 27 reflects all or nearly all rays which issue from the rear portion of the source 26 and directs such rays toward the exit opening 2A.

The housing 24 further contains customary auxiliary equipment 29 (e.g., timer means, chokes, etc.) and the controls 30.

Figure 17:
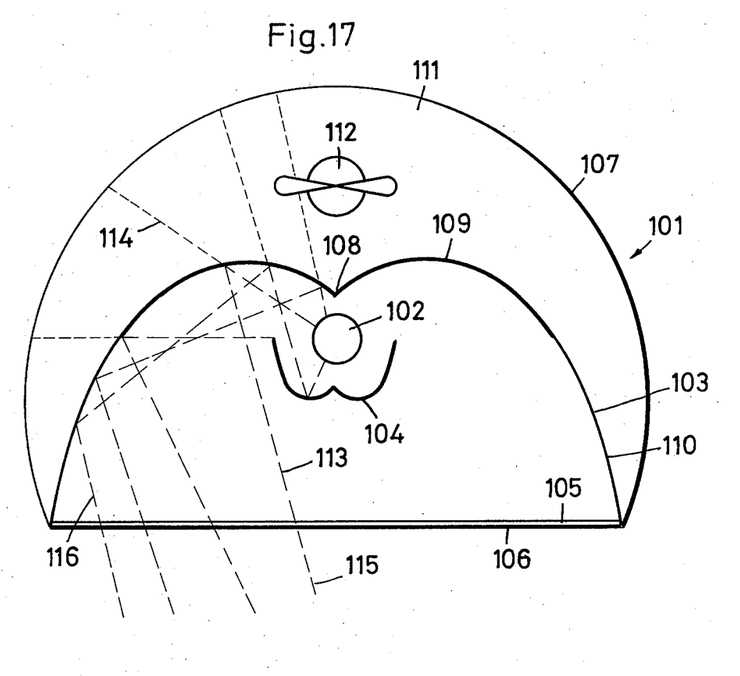
FIG. 17 is a schematic sectional view of a twelfth apparatus.

The high-pressure mercury lamp 26 can be replaced with a Xenon lamp and the filter 25 may constitute (or may be combined with) a plate which intercepts heat but permits the UVA band of ultraviolet radiation to reach the area of the field 13A. Alternatively, the reflector 27 may be of a type which reflects ultraviolet radiation but permits passage of at least some light and heat which latter is then withdrawn from the space behind the reflector (for example, in a manner as shown in FIG. 17). The provision of such reflectors is desirable if the radiation sources constitute high-pressure mercury lamps or Xenon lamps which produce substantial amounts of light and/or heat energy (see FIG. 4).

Still further, the apparatus of FIG. 5 can be modified by using a reflector which reflects only ultraviolet light and is disposed at an angle of 20° to 50° to incident radiation. The reflector reflects ultraviolet radiation laterally toward the area where the high-density field is readily accessible to a person and permits at least a very high percentage of light and heat to pass therethrough. It has been found that such apparatus are a more effective means for preventing exposure of a person to excessive amounts of heat energy than those apparatus wherein the heat absorbing or intercepting means is installed in the exit opening. Another advantage of the apparatus of FIG. 5 is that the eyes of a person standing or sitting in the region of the high-density radiation field are shielded from bright light.

The source 26 of FIG. 5 is preferably a lamp with an UVA radiation output of at least 20 watts, and the angle of divergence of the front portions of side walls of the reflector 27 is preferably at least 80°, most preferably at least 100°. Such wide-angle reflector is capable of insuring uniform distribution of reflected ultraviolet radiation as well as the development of a relatively large high-density field 13A close to the exit opening 2A. The overall radiation output of a high-pressure mercury lamp or Xenon lamp which can furnish at least 20 watts in the UVA band of ultraviolet radiation is normally between 1,000 and 2,000 watts. The apparatus of FIG. 5 can be designed to insure simultaneous tanning of the face, shoulders and the upper part of the torso of a person sitting or standing in front of the exit opening 2A.

Figure 6:
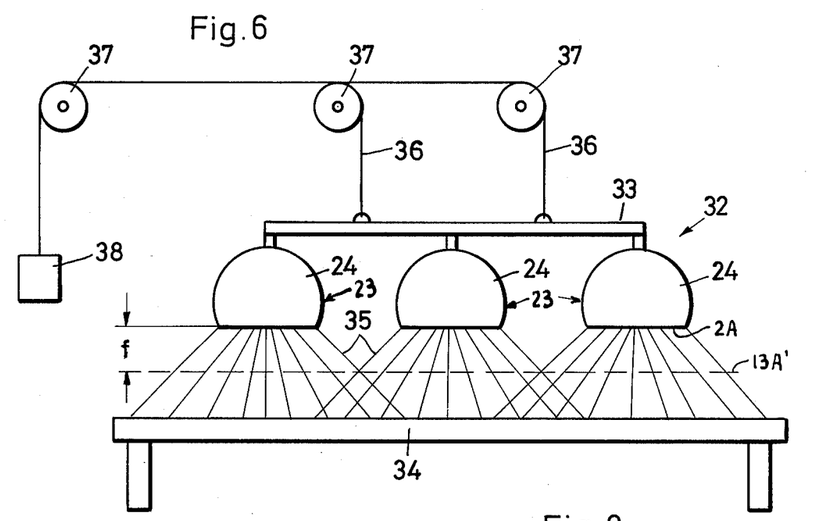
FIG. 6 is a schematic side elevational view of a third apparatus.

The apparatus 32 of FIG. 6 can be mounted on the ceiling or on a wall of a room and comprises three discrete sunlamps or units 23 which may but need not be identical with the apparatus 23 of FIG. 5. Each unit 23 comprises a hollow spherical housing 24 with an exit opening 2A facing a cot, bed, bunk or couch 34 therebelow. The housings 24 are suspended on a horizontal carrier 33 which is attached to the adjacent ends of cords, cables or analogous flexible elements 36. The flexible elements 36 are trained over pulleys 37 and their other ends are connected to a counterweight 38 or a winch (not shown) which enables a person to change the distance between the housings 24 and the bed 34 with a minimum of effort or by starting a reversible motor for the winch.

The distances between neighboring housings 24 are selected in such a way that the outermost rays 35 issuing from the radiation sources (not shown) of the respective units 23 cross each other at a distance $f = 10-30$ centimeters from the exit openings 2A. This is the region where the density of the radiation field 13A' is most satisfactory for a person occupying the bed 34.

The units 23 are lifted to afford convenient access to a patient who wishes to occupy the bed 34, to enable the patient to leave the bed 34, and/or to change the level of the radiation field 13A' during or preparatory to treatment.

It has been found that three units of the type shown in FIG. 5 normally suffice to develop a field 13A' which is large enough to allow for simultaneous tanning of the entire body. It is clear that the units 23 of FIG. 6 can be mounted one above the other so that a person can stand in front of the apparatus. Also, the carrier 33 of FIG. 6 can be mounted in such a way that it is movable between the illustrated horizontal position for treatment of a person on the bed 34 or to a vertical position in which the units 23 are located one above the other to enable a standing patient to take a sunbath.

The UVA radiation output of a rod-shaped Xenon lamp is normally at least 50 watts per meter. Such lamps can be used in the apparatus of FIG. 5 or 6. Each Xenon lamp is associated with a discrete reflector (e.g., a reflector 27) and its overall output normally exceeds 1,000 watts. The overall output of a Xenon lamp having a length of 40 centimeters is normally between 1,500 and 2,500 watts, and the overall output of a Xenon lamp having a length of 150 centimeters is normally in the range of 9,000 watts.

The radiation-intercepting action of the plate-like filter 25 of FIG. 5 (and of the corresponding filters in the units 23 of FIG. 6) can be taken over by the tubular envelopes of the respective radiation sources. The filter or filters 25 can be mounted in such a way that they can be moved into and away from the respective exit openings, for example, in order to allow for short-lasting exposure of skin to radiation in the entire range of ultraviolet light.

The bed 34 insures that a patient whose body is resting thereon invariably assumes an optimum position with respect to the units 23, i.e., with respect to the high-density radiation field 13A'. This enhances the effectiveness of the apparatus because the patient is compelled to maintain his or her body at an optimum distance from the exit openings 2A. The same effect can be achieved if the units 23 are mounted one above the other, for example, by providing an upright partition in front of which the patient stands while his or her skin is exposed to ultraviolet radiation in the range of 315- to 400 nm.

Figure 7:
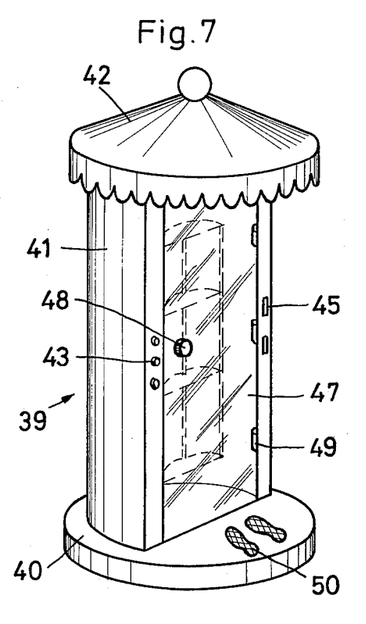
FIG. 7 is a perspective view of a fourth apparatus.

The apparatus 39 of FIG. 7 resembles a kiosk or tower and includes a substantially semicylindrical housing 41 mounted on a round base plate 40 and having a roof 42. The front side of the housing 41 can be closed by a glass door 47 which is mounted on hinges 49 and has a knob 48. The controls 44 (FIG. 8) include one or more actuating knobs 43 which are mounted at the front side of the housing 41 adjacent the knob 48. The apparatus 39 is assumed to be used in a public or private bath, in a gymnasium, clinic, hospital or a similar institution and has one or more slots 45 for insertion of coins which actuate a coin-operated starter 46 shown in FIG. 8. The housing 41 further contains the customary auxiliary equipment 53.

Figure 8:
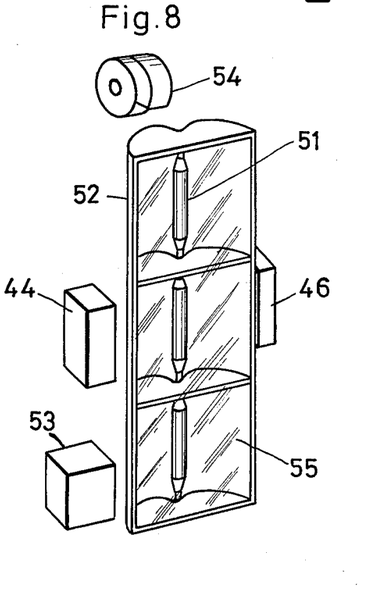
FIG. 8 is a schematic perspective view of certain details in the apparatus of FIG. 7.

The space behind the door 47 contains three roof-shaped wide-angle reflectors 52 for three aligned upright rod-shaped radiation sources 51 (e.g., Xenon lamps). The door 47 constitutes a filter for the UVB and UVC bands of ultraviolet radiation. For example, each source 51 may have a length of 60 centimeters and an output of 4,000 watts. The arrangement is such that a high-density radiation field develops at a distance of approximately 20 centimeters from the front side of the door 47. In order to enable the user to assume an optimum position with respect to the sources 51, the base plate 40 is formed with indicia 50 in the form of foot prints. The width of the aforementioned radiation field may be approximately 70 centimeters and the height of the field may be approximately 180 centimeters. This enables a person standing on the indicia 50 to expose the entire front or rear side of his or her body to ultraviolet radiation.

The housing 41 preferably further contains a blower 54 or another suitable cooling device which withdraws heat from the space between the door 47 and the fixedly mounted heat shields or panes 55 in front of the reflectors 52. The shields 55 can be omitted if the blower 54 is capable of removing sufficient quantities of heat to insure that the temperature in the region where a person stands (on the indicia 50) is within a range which is below the range of discomfort to the person. As a rule, heat shields and/or one or more blowers will be needed if the sources 51 are Xenon lamps because such sources generate substantial quantities of heat energy.

If the patient wishes to expose (preferably for a short interval of time) his or her body to ultraviolet rays in the entire range between 200 and 400 nm, the door 47 is simply opened before the patient steps on the indicia 50. The blower 54 is then less effective but the fixedly mounted shields 55 continue to intercept substantial amounts of heat energy. The door 47 can be replaced with a suitably inclined mirror which is designed to reflect ultraviolet rays in the UVA band in a desired direction but does not reflect heat.

Short-lasting opening of the door 47 might be desirable to build vitamin D, to immunize the patient against certain illnesses, to raise the amount of precursors of melamin, to promote the circulation of blood and/or to produce other beneficial effects. The controls of the apparatus of FIG. 7 can be designed in such a way that the door 47 is automatically opened for a preselected interval of time in response to insertion of one or more coins into the slot or slots 45, especially if the door 47 is mounted in such a way that can open or close while the patient stands on the base plate 40.

Figure 9:
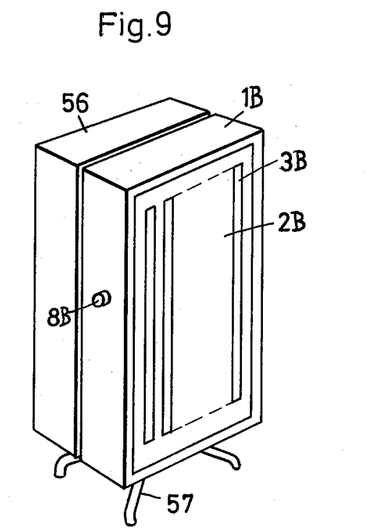
FIG. 9 is a perspective view of a fifth apparatus.

FIG. 9 shows a further apparatus having a housing 1B with a window or exit opening 2B in front of upright parallel rod-shaped radiation sources 3B. The starter knob is shown at 8B. The rear portion 56 of the apparatus constitutes a framed mirror, a shelf or another piece of furniture which is attached to the rear side of the housing 1B and is mounted therewith on a common pedestal 57 in such a way that the housing 1B and the piece of furniture 56 can be rotated (at least through 180°) about a vertical axis. When the apparatus is not in use (for tanning), the piece of furniture 56 is moved in front to afford access to the contents of the shelf and/or to permit the use of the mirror. The sources 3B are assumed to constitute low-pressure mercury lamps.

Figure 10:
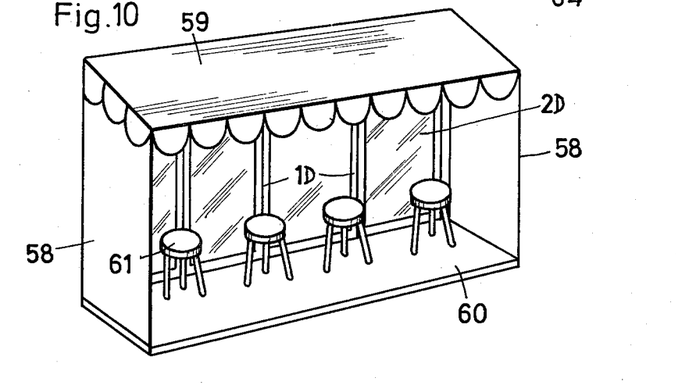
FIG. 10 is a perspective view of a sixth apparatus.

The apparatus of FIG. 10 can be used simultaneously by several persons and can be termed a "tanning bar". This apparatus includes four units of the type shown in FIG. 1 and a veranda- or portico-like structure which confines the four housings 1D and has a floor 60, two side walls 58 and a roof 59. The stools 61 on the floor 60 can be occupied by persons desirous of acquiring a tan. Each of the stools 61 can be placed in front of a discrete window or exit opening 2D and can be shifted to a position in which a selected part of the body is located in the maximum-density radiation field of the respective unit. If desired, the stools 61 can be fixed to the floor 60 in optimum positions with respect to the radiation fields which are produced by the respective units.

Figure 11:
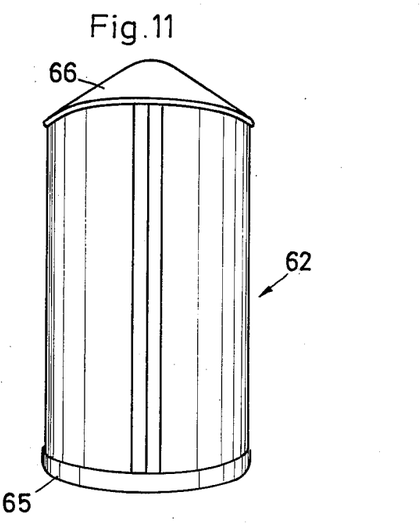
FIG. 11 is a perspective view of a seventh apparatus.
Figure 12:
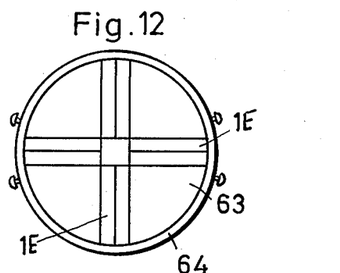
FIG. 12 is a plan view of the apparatus of FIG. 11, with the roof removed.

FIGS. 11 and 12 show an apparatus 62 which is somewhat similar to the apparatus of FIG. 7; however, it comprises four units each having a housing 1E and each installed in a separate cell or cabin 63 adapted to be closed by an arcuate door 64. The pivotable doors 64 can be replaced by curtains or folding doors. The apparatus comprises a base plate 65 and a roof 66. Each cabin 63 is flanked by two units having housings 1E so that a person occupying a selected cabin is exposed to ultraviolet radiation from two sides. Two neighboring housings 1E are disposed back-to-back and the housings 1E flanking a cabin 63 make an angle of 90°.

It is clear that the apparatus of FIGS. 11 and 12 can be modified by reducing the number of cabins to three or two, or by increasing the number of cabins to five or more.

Figure 13:
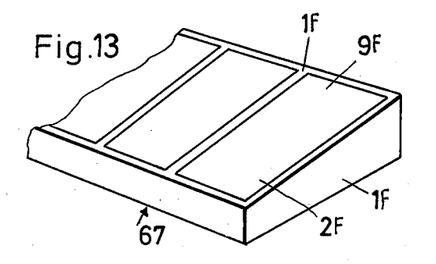
FIG. 13 is a perspective view of a portion of an eighth apparatus.

FIG. 13 shows a further apparatus 67 which has several housings 1F mounted on the floor, side-by-side, and having windows or exit openings 2F which are slightly inclined with respect to a horizontal plane. The windows 2F contain panes 9F which may constitute filters for the UVB and UVC bands of ultraviolet radiation and which are preferably sturdy enough to support the body of a person lying or sitting thereon. The apparatus 67 can be assembled of several discrete units, or the housings 1F may be made integral with each other. Also, the apparatus 67 may be provided with wheels or the like to facilitate transport to different locales of use or to storage.

The apparatus of FIG. 13 automatically insures that the person resting on one of the filters 9F is located at an optimum distance from the radiation source or sources. In such apparatus, the plane of the maximum-density radiation field preferably coincides with or is very closely adjacent to the plane of the respective filter.

Figure 14:
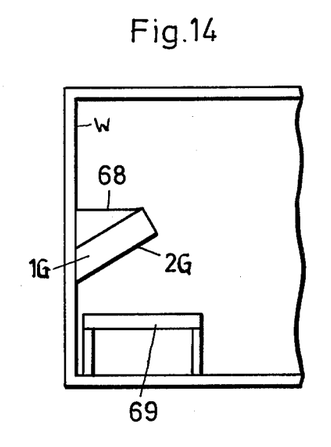
FIG. 14 is a schematic end elevational view of a ninth apparatus.

Referring to FIG. 14, there is shown an apparatus which is mounted on a wall W above a bed or bunk 69. The housing is shown at 1G and its window or exit opening at 2G. The window faces downwardly and is slightly inclined with respect to a horizontal plane. The housing 1G is mounted on a frame 69 which is permanently or separably secured to the wall W. The illustrated inclination of the window 2G is advantageous because the user has ample room to lie down on or to rise from the bed 69. The length of rod-shaped radiation sources (not shown) in the housing 1G is preferably sufficient (e.g., 150 to 180 centimeters) to allow for simultaneous exposure of the entire body to ultraviolet radiation in the UVA band.

Figure 15:
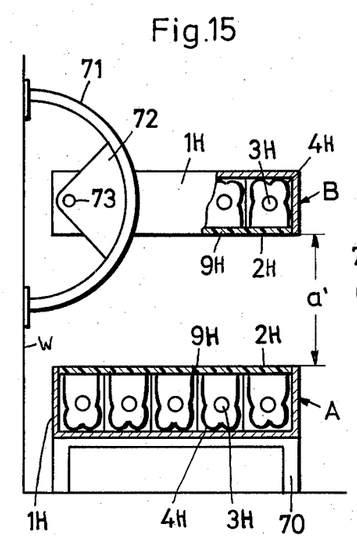
FIG. 15 is a schematic partly end elevational and partly vertical sectional view of a tenth apparatus with two units located one above the other.

The apparatus of FIG. 15 comprises a lower unit A and an upper unit B. Each of these units has a sheet metal housing 1H which contains several radiation sources 3H each having a length of 180 centimeters. The associated reflectors are shown at 4H.

The lower unit A is mounted on a support 70 and can be said to form part of a cot, bed, couch or bunk on which a person can rest during exposure of his or her skin to ultraviolet radiation. The ends of the upper unit B are secured to a wall W by semicircular brackets 71 having plates 72 for a pivot 73 which carries the upper housing 1H. The upper housing 1H is pivotable about the horizontal axis of the member 73 so as to change the inclination of exit openings or windows 2H and panes or filters 9H with respect to the lower unit A. Means (not shown) is provided to releasably hold the upper unit B in a selected angular position. The illustrated angular position (in which the windows 2H of the upper unit B are located in a horizontal plane) has been found to be an optimum position. The distance $a'$ between the planes of the upper and lower windows 2H may be in the range of 40 to 60 centimeters. This normally suffices to enable a person to lie down on the unit A and have his or her body exposed to radiation issuing from the units A and B. It is clear, however, that the apparatus of FIG. 15 may comprise controls which enable the user to turn on the unit B independently of the unit A or vice versa.

The apparatus of FIG. 15 may comprise a third unit which can be mounted on the wall W so that a person resting on the unit A is exposed to ultraviolet radiation from below, from above, as well as from one side. The third unit may but need not be identical with the unit A or B.

Figure 16:
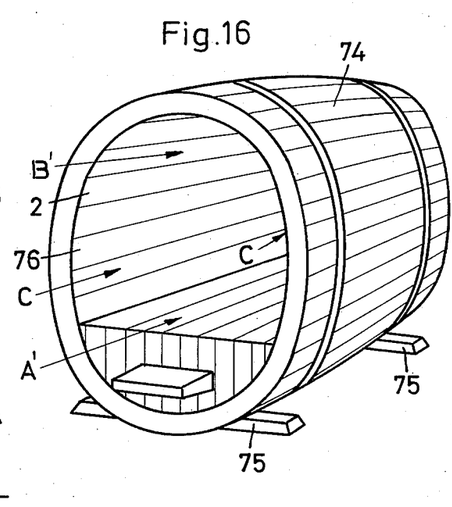
FIG. 16 is a perspective view of an eleventh apparatus which resembles a barrel.

The apparatus 74 of FIG. 16 resembles a horizontal barrel which is mounted on legs 75. The interior of the apparatus comprises a lower unit A' which may be analogous to or identical with the unit A of FIG. 15, and an upper unit B' which forms part of the upper portion of the apparatus. The apparatus further includes two additional (lateral) units C. Each unit comprises several parallel rod-shaped radiation sources associated with reflectors and mounted behind elongated strip-shaped filters 76 made of glass or other material which intercepts certain bands of ultraviolet radiation. The filters 76 of the units C and B' together form an internal liner of the barrel and the liner extends along an arc of at least 180°. The liner may form part of a circular cylinder, a cylinder having an oval shape or a cylinder which has a more or less pronounced polygonal cross-sectional outline. In each instance, the body of a person occupying the unit A' is exposed to ultraviolet radiation from all sides. The exit openings of the reflectors in the units A', B' and C are shown at 2K.

Referring finally to FIG. 17, there is shown an apparatus 101 which comprises a rod-shaped radiation source 102, a trough-shaped reflector 103, an auxiliary reflector 104 in front of the source 102, a substantially cylindrical housing 107 with an exit opening 106, and a plate-like filter 105 in the opening 106.

The reflector 103 consists of two halves which are mirror symmetrical to each other with respect to a plane including the axis of the source 102 and extending at right angles to the plane of the filter 105. The central portion of the rear wall of the reflector 103 has a pronounced notch 108 which is closely adjacent the rear side of the source 102. The rear wall and the rear portions of the side walls of the reflector 103 constitute mirrors or are coated with reflecting material for ultraviolet radiation (indicated by a heavy line 109), and the front portions of the side walls of the reflector diverge toward the exit opening 106. Each of the two halves of the reflector 103 has a concave inner surface which begins at the respective side of the exit opening 106 and ends at the notch 108. The space 111 between the rear side of the reflector 103 and the housing 107 constitutes a cooling zone wherein air is circulated by one or more blowers 112 or the like.

It is assumed that the source 102 of FIG. 17 is a Xenon lamp. As indicated by the curve V of FIG. 4, such lamp emits ultraviolet radiation mainly in the UVA band (between 315 and 400 nm). FIG. 4 further shows that the lamp 102 emits substantial amounts of radiation in the range of visible and infrared light. Therefore, The mirrored portion 109 of the reflector 103 of FIG. 17 is designed to reflect primarily ultraviolet radiation (see the ray 113) but to permit passage of heat (see the ray 114) so that heat energy can be withdrawn from the zone 111 by turning on the blower 112. Light which passes through the reflector portion 109 is reflected by the housing 107 and is also converted into heat energy which is withdrawn by the blower 112. The filter 105 intercepts the bands UVA and UVC so that only the band UVA (see the ray 115) advances beyond the window 106 and reaches the skin of a person who is located in front of the housing 107. The portion 109 of the reflector 103 reflects those rays (shown at 116) which issue from the rear side of the source 102 and directs such rays toward the exit opening 106. Each ray 116 can be reflected once or more than once. The auxiliary reflector 104 intercepts light and heat radiation which would be annoying to a person facing the window 106. Furthermore, the reflector 104 insures that all rays which are not immediately directed toward the reflector 103 are reflected onto the portion 109 which permits the light and heat rays to pass and reflects only ultraviolet rays. The reflector 104 thus insures that radiation issuing from the front half of the source 102 cannot propagate itself directly toward the window 106 but is reflected toward the main reflector 103 which reflects only ultraviolet radiation whereby the ultraviolet rays travel toward the filter 105 which permits the band UVA to reach the patient. The density of the relatively large radiation field which develops in front of the exit opening 106 is very pronounced, and such field consists exclusively or almost exclusively of UVA radiation. Thus, the percentage of light rays, infrared rays and ultraviolet rays in the UVB and UVC bands is negligible.

The improved apparatus is susceptible of many additional modifications without departing from the spirit of the invention. For example, the apparatus shown in FIGS. 8 to 15 can utilize radiation sources in the form of high-pressure mercury lamps (FIGS. 5 and 6) or Xenon lamps (FIGS. 7 and 8). Furthermore, the apparatus or one or more of its units can be installed in the niche or niches of a wall. Still further, the apparatus may be installed in the corner of a room and its door or doors may constitute one or more mirrors which can be used when the doors are closed. Also, the controls of the apparatus may be programmed so that the apparatus is turned on, operated for a selected period of time, and turned off in automatic response to actuation of a single knob or the like. The programming may be such that the filter or filters for the UVB and UVC bands can be moved away for a given period of time at the start of a treatment and are thereupon returned to operative positions in a fully automatic way. Moreover, the tubular envelopes of the radiation sources can constitute filters which replace the platelike filter 105 of FIG. 15 and the corresponding filters in other embodiments of the apparatus.

It is further clear that the improved apparatus can be used for other purposes, i.e., not only for artificial tanning of human skin. For example, the high-density field which consists (exclusively or nearly exclusively) of ultraviolet radiation in the UVA band can be used for therapeutical purposes and/or to produce other beneficial effects.

Extensive experimentation with the improved apparatus indicates that the high-density field or fields are preferably located at a distance of 0 to 30 centimeters from the exit opening or openings, most preferably at a distance between 10 and 20 centimeters. The density of the radiation field is at least 4 mw/cm$^2$, preferably between 5 and 30 mw/cm$^2$ and most preferably about 15 mw/cm$^2$. In a table model, the area of the field is in the range of 0.2 m$^2$. In a solarium, the area of the field is preferably at least 0.5 m$^2$ (e.g., the field may have a length of at least 120 centimeters and a width of at least 50 centimeters).

Certain radiation sources which are presently available on the market and can be used in the apparatus of the present invention include low-pressure mercury lamps of the type TL/05 or TL/09 produced by Philips, high-pressure mercury lamps of the type PQ produced by Sueddeutsche Metallwerke of Federal Republic Germany, and Xeonon lamps of the type XOP 25 produced by Philips.

As mentioned above, the tanning effect upon human skin is produced primarily by ultraviolet radiation in the UVA band between 315 and 400 nm. Furthermore, the tanning begins when the amount of radiation within the range of 315 to 400 nm reaches or exceeds a predetermined (relatively high) threshold value. Such threshold value depends on the nature of skin and is normally between 7.5 and 10 mw per square centimeter. The improved apparatus insures that the threshold value is exceeded within a relatively short interval of time by rendering it possible that a person can stand, sit or lie close to the exit opening or openings, i.e., at a distance which is only a small fraction of the distance prescribed in connection with conventional sunlamps. In fact, and as pointed out above, a person can be positioned immediately adjacent the exit opening or openings. This insures that the density of the radiation field in which the human skin is located is very high. At the same time, the filter means of the radiation source or sources and/or discrete filter means in, in front of, or behind the exit opening or openings protect the skin from sunburn by preventing radiation in the 200 to 315 nm range from reaching the skin. In conventional sunlamps, the likelihood of sunburn increases if the person moves nearer to the exit opening. The amount of heat energy which reaches the skin during treatment can be kept within a range which is below the range of discomfort to the person using the apparatus by resorting to low-output radiation sources and/or by resorting to heat absorbing means of any suitable design. This enables the person using the apparatus to remain close to the exit opening or openings for extended periods of time, not only because the person is protected from sunburn but also because the intensity of heat is sufficiently low to enable such person to stand the treatment for as long as necessary, e.g., to acquire a pronounced tan in the course of a single treatment.

Since the area of the high-density radiation field decreases if the field is produced close to the exit opening or openings, the improved apparatus can use two or more radiation sources and an equal number of reflectors to establish a field having an area which suffices to expose the selected portion or portions of or the entire body of a person to the UVA band of ultraviolet radiation, also in such a way (see, for example, FIG. 12, 15 or 16) that the body is exposed to radiation coming from two or more sides. The just mentioned advantageous feature of the apparatus can be achieved by appropriate selection of the number, orientation, distribution and dimensions of the radiation sources and/or associated reflectors.

Experiments with the improved apparatus indicate that a pronounced tanning effect, at a density of 4 mw per square centimeter, can be achieved by continuous exposure of skin to UVA radiation for a period of 30 minutes. The period of treatment can be reduced by increasing the density of the field to 5–30 mw per square centimeter. If the density is reduced below 4 mw/cm$^2$ (e.g., to 2 mw/cm$^2$), the treatment (which can be broken up into two or more sessions) takes longer (e.g., 1 hour). The just mentioned periods can be shortened by reducing the threshold value of tanning effect of UVA radiation by suitable sensitizing means.

The breaking up of treatment into two or more sessions is optional because a continuous treatment is neither uncomfortable nor dangerous to the patient or patients. For example, a person who wishes to acquire a pronounced tan and can afford to spend a relatively long period of time in front of, above or below one or more radiation sources can resort to a single session. On the other hand, a person who does not wish to acquire a pronounced tan in a single day will break up the treatment into two or more sessions. The improved apparatus can be set up in public areas, such as baths, hotels, motels, guesthouses, airline terminals, recreation rooms of hospitals or schools, assembly rooms of community centers and many others. As a rule, a person who desires to acquire a pronounced tan will prefer to achieve his or her objective in a single session or in a small number of (e.g., two or three) sessions. Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

What is claimed is:

1. Apparatus for producing ultraviolet radiation, particularly a quick-tanning sunlamp, comprising at least one source of substantially uniform ultraviolet radiation including at least five closely adjacent rod-shaped low-pressure mercury lamps; reflector means associated with said source and defining at least one exit opening for ultraviolet radiation, said reflector means including a discrete trough-shaped reflector for each of said lamps and each of said reflectors surrounding the respective lamp along an arc of at least 180°, said source and said reflector means being constructed and assembled to establish a high-density radiation field of predetermined area in the region of said exit opening and the heat output of said lamps being sufficiently low to insure that the temperature in the region of said field is within a range which is below the range of discomfort to a person exposed to said field; and means for intercepting at least the major percentage of wavelength bands of ultraviolet radiation below approximately 315 nm ahead of said field so that said field consists essentially of the remaining wavelength band of ultraviolet radiation.

2. Apparatus as defined in claim 1, wherein the output of said lamps in said remaining band is at least 5 watts per meter.

3. Apparatus as defined in claim 1, wherein the number of said lamps is between five and twenty.

4. Apparatus as defined in claim 1, wherein the number of said lamps is between ten and twelve.

5. Apparatus as defined in claim 1, wherein the output of each of said lamps in said remaining band is at least 8 watts per meter.

6. Apparatus as defined in claim 1, wherein each of said lamps has a length in excess of 100 centimeters.

7. Apparatus as defined in claim 6, wherein the length of each of said lamps is approximately 150 centimeters.

8. Apparatus as defined in claim 6, wherein the length of each of said lamps is approximately 180 centimeters.

9. Apparatus as defined in claim 1, wherein each of said lamps contains a chemical additive which maintains the output in said remaining band and the relative spectrum constant regardless of temperature changes.

10. Apparatus as defined in claim 9, wherein said additive is an amalgam.

11. Apparatus as defined in claim 1, wherein the diameter of each of said lamps at least equals the distance between two neighboring lamps.

12. Apparatus as defined in claim 1, wherein each of said reflectors has a rear wall located behind the respective lamp and remote from said exit opening, and two side walls flanking the respective lamp and having front portions extending forwardly toward said opening and beyond the respective lamp.

13. Apparatus as defined in claim 12, wherein the front portions of said side walls have substantially parallel inner surfaces which face each other.

14. Apparatus as defined in claim 12, wherein the side walls of said reflectors define relatively narrow gaps with the respective lamps and the configuration of the rear wall of each of said reflectors is such that at least the major percentage of radiation issuing from a lamp and impinging upon the respective rear wall is reflected into the respective gaps.

15. Apparatus as defined in claim 14, wherein each of said reflectors consists of two identical halves which are mirror symmetrical to each other with reference to a plane including the axis of the respective lamp and halving the respective rear wall.

16. Apparatus as defined in claim 15, wherein each of said rear walls has a front surface including two concave portions disposed at the opposite sides of the respective plane and each arranged to reflect radiation into the respective gap.

17. Apparatus as defined in claim 16, wherein each of said reflectors further comprises two intermediate walls located between the rear wall and the side walls thereof and having concave inner surfaces, each of said side walls further having a rear portion provided with a concave inner surface, the radiation which issues from a lamp and impinges upon the inner surface of the rear portion of a side wall of the respective reflector being reflected against the concave inner surface of the remote intermediate wall and thence into the respective gap.

18. Apparatus as defined in claim 17, wherein the radii of curvature of the concave inner surfaces of said intermediate walls are smaller than the radii of curvature of the concave portions of said front surfaces and the radii of curvature of the concave inner surfaces of said rear portions.

19. Apparatus as defined in claim 1, wherein said lamps have a tubular envelopes which constitute said intercepting means.

20. Apparatus as defined in claim 19, wherein said envelopes consist of glass.

21. Apparatus as defined in claim 1, wherein said intercepting means is located in said exit opening.

22. Apparatus as defined in claim 1, wherein said intercepting means is a filter which is movable into and from the path of radiation between said source and said field.

23. Apparatus as defined in claim 1, wherein said field is located in a substantially vertical plane and is large enough to allow for exposure of the entire body of an adult to ultraviolet radiation in said remaining band.

24. Apparatus as defined in claim 1, wherein said source and said reflector means define two exit openings disposed in planes making an angle of less than 180°.

25. Apparatus as defined in claim 24, wherein said angle is approximately 90°.

26. Apparatus as defined in claim 24, wherein each of said openings consists of several coplanar smaller openings.

27. Apparatus as defined in claim 1, comprising a first unit and a second unit located below said first unit, each of said units having a source and reflector means therefor, the exit opening of said first unit facing downwardly toward said second unit and the exit opening of said second unit facing upwardly toward said first unit, said exit openings being spaced apart from each other sufficiently to provide room for the body of a person therebetween.

28. Apparatus as defined in claim 27, wherein the intercepting means of said second unit includes a plate-like filter which is installed in the respective exit opening and provides a support for the body of a person between said exit openings.

29. Apparatus as defined in claim 1, comprising an upper unit having a downwardly facing exit opening, a lower unit having an upwardly facing exit opening spaced apart from the opening of said upper unit and at least one third unit between said upper and lower units and having an exit opening facing toward the space between the exit openings of said upper and lower units, each of said units having a discrete source, discrete reflector means for the source, and discrete intercepting means for said predetermined bands.

30. Apparatus as defined in claim 1, further comprising a bed, said source and said reflector means being located at a level above said bed and said exit opening facing downwardly toward said bed.

31. Apparatus as defined in claim 30, further comprising means for moving said source and said reflector means up and down toward and away from said bed.

32. Apparatus as defined in claim 30, wherein said exit opening is located in a plane which is at least slightly inclined with respect to a horizontal plane.

33. Apparatus as defined in claim 1, further comprising a common housing for said source, said reflector means and said intercepting means.

34. Apparatus as defined in claim 33, wherein said housing constitutes or forms part of a piece of furniture.

35. Apparatus as defined in claim 33, wherein said housing is a tower.

36. Apparatus as defined in claim 33, wherein said housing is a patio.

37. Apparatus as defined in claim 33, wherein said housing is a barrel.

38. Apparatus as defined in claim 33, further comprising a pedestal for said housing, said housing being movable relative to said pedestal.

39. Apparatus as defined in claim 1, wherein said exit opening is substantially horizontal and further comprising means provided in said exit opening and arranged to support a human body thereon at a level above said source.

* * * * *